United States Patent [19]

Doerschner

[11] Patent Number: 4,758,229

[45] Date of Patent: Jul. 19, 1988

[54] NEEDLE-STICK INJURY PREVENTION DEVICE AND METHOD

[75] Inventor: David L. Doerschner, Rolling Meadows, Ill.

[73] Assignee: Hollister Incorporated, Libertyville, Ill.

[21] Appl. No.: 100,096

[22] Filed: Sep. 24, 1987

[51] Int. Cl.[4] .................................... A61M 5/00

[52] U.S. Cl. .................................... 604/187; 206/63.3; 206/365

[58] Field of Search ............... 604/187, 162, 163, 110; 206/63.3, 364, 365, 524.2, 813, 828, 484, 484.1, 460, 438; 128/DIG. 26; 229/87 R

[56] References Cited

U.S. PATENT DOCUMENTS

| | | | |
|---|---|---|---|
| 3,727,658 | 4/1973 | Eldridge, Jr. | 206/63.3 |
| 3,940,873 | 3/1976 | Lawless | 206/63.3 |
| 3,944,069 | 3/1976 | Eldridge, Jr. | 206/63.3 |
| 4,589,552 | 5/1986 | Chevalier | 229/87 R |

*Primary Examiner*—John D. Yasko
*Attorney, Agent, or Firm*—Tilton, Fallon, Lungmus

[57] ABSTRACT

A device and method for protecting users of hypodermic needle and syringe assemblies from accidental needle-stick injuries in the handling of such assemblies following use thereof and for facilitating the safe disposal of such assemblies. The device comprises a pad of relatively soft sheet material, preferably a sheet of closed-cell plastic foam, having an upper surface coated with a pressure-sensitive adhesive. A shield or patch of tough, imperforate, foldable material is secured to the upper surface of the pad in such a way that the adhesive-coated surface of the pad defines a border zone extending outwardly about the entire perimeter of the shield. A fold line, preferably defined in part by a preformed crease in the shield, extends along the midlines of the pad and shield so that a used syringe may be adhesively secured to the pad with the syringe axis lying along the midline of the pad and the tip of the syringe needle located along the midline of the shield. When the pad is folded about the syringe, the needle is encased between the folded side walls of the shield which in turn are held together by portions of the pad's adhesive-coated upper surface brought into sealing engagement with each other about the periphery of the shield.

14 Claims, 2 Drawing Sheets

10
15
12
15
11
13

10
15
12
15
11
13

3
3
14
15a
15
16
15b
11
12
11c
11d 16
15
11b
12
11
11a 15
15a
17
S
15b
12
11
18
11c
14
11d 11
12
11c
11d
15a
15b
17
16

6
15
11a
17
7
11
11d
S
11c
6
7
18

11
11c
11d
12
18

NEEDLE-STICK INJURY PREVENTION DEVICE AND METHOD

BACKGROUND AND SUMMARY

Concerns have been expressed over the frequent occurrence of accidental needle-stick or needle-prick injuries by health care providers because, even though disease from such injuries is rare, there is always the possiblity that such a disease might be transmitted and be lethal. It has been established that the risk of acquiring hepatitis B from accidental injury involving HBsAg-positive blood is 26% and that the risk of transmission of acquired immune deficiency syndrome is somewhat less than that. A. D. Nixon et al, The Lancet, pp. 888–9, Apr. 9, 1986.

It is now known that a substantial proportion of needle-stick injuries occur when a hypodermic needle is being recapped or resheathed. Center for Disease Control guidelines recommend that needles never be recapped and that all used needle/syringe assemblies be discarded into disposal units. In practice, such guidelines are often disregarded in the complex and busy hospital environment, creating the further risk of possible re-use of discarded syringes and needles by drug abusers.

While efforts have been made to develop simple, inexpensive, and convenient devices for reducing the dangers posed by used syringe assemblies, it appears that the use of such protective devices has presented, to a greater or lesser extent, the same risks involved in the recapping of used needles. Examples of such devices may be found in U.S. Pat. Nos. 2,270,536, 3,712,302, 4,273,123, 3,796,359, 3,820,852, 4,592,744, 4,332,323, 3,944,069, and 4,182,448. The problem of reducing the dangers of accidental needle sticking while disposing of used hypodermic needles is specifically addressed in U.S. Pat. Nos. 4,573,975, 4,610,667, and 4,596,562, but such devices all require axial or endwise movement of a used, unsheathed needle toward a receiving target supported by the user's other hand, to that extent, a significant risk remains.

An important aspect of this invention therefore lies in providing a relatively simple and inexpensive device that may be easily handled by a user to encase a used syringe and needle assembly and, in particular, that may be manipulated in use without requiring any endwise movement of the needle tip towards a user's hand. The device may be stored in flat condition and is readily foldable so that, for example, several such devices may be easily carried in a user's pocket prior to use. Despite its deformability, the device includes a portion that takes on increased stiffness when folded in use. That portion defines a tough, protective enclosure for the needle tip, and the needle is prevented from escaping from such enclosure because of the adhesive seal between folded wall portions of the device and between those wall portions and syringe itself. Once enclosed within the folded device, a syringe may be safely discarded with the tip of the needle effectively shielded to avoid injury.

Briefly, the device takes the form of a pad of soft, foldable sheet material, preferably an easily-deformable, fluid-impermeable material such as a closed-cell plastic foam, having upper and lower surfaces and having a pair of lateral sections disposed on opposite sides of the pad's longitudinal midline. A coating of pressure-sensitive adhesive extends over the upper surface, and a protective shield or patch of tough, flexible, imperforate sheet material is secured to a relatively small area of that upper surface. Ideally, the shield has a pre-formed crease aligned with the midline of the pad. In use, the barrel of a used syringe is shifted laterally into contact with the adhesive coating and is adhered to that coating to immobilize the syringe on the pad with the needle tip overlying the protective shield. Thereafter, the pad and shield are folded to encase the needle tip between adjacent side sections of the shield and to urge portions of the adhesive-coated surface of the pad into sealing contact with each other about the syringe and about the periphery of the folded shield. At no time during such immobilizing and folding operations does endwise movement of the needle tip towards a user's hand become necessary; the syringe assembly may be shifted by lateral movement into its secured position on the pad, and the folding operations only require finger movements in directions transverse to the axis of the syringe. Although the thin protective shield is readily folded along its crease line, once that step has occurred the fold performs a stiffening or reinforcing function that enhances the protective action of the shield. Such reinforcement, along with the extensive areas of adhesive contact between the folded side portions of the pad, and between those portions and the syringe itself, effectively prevent escape or protrusion of the needle tip from its containment.

Other advantages, features, and objects of the invention will become apparent from the specification and drawings.

DRAWINGS

DETAILED DESCRIPTION OF PREFERRED EMBODIMENT

Figure 1:
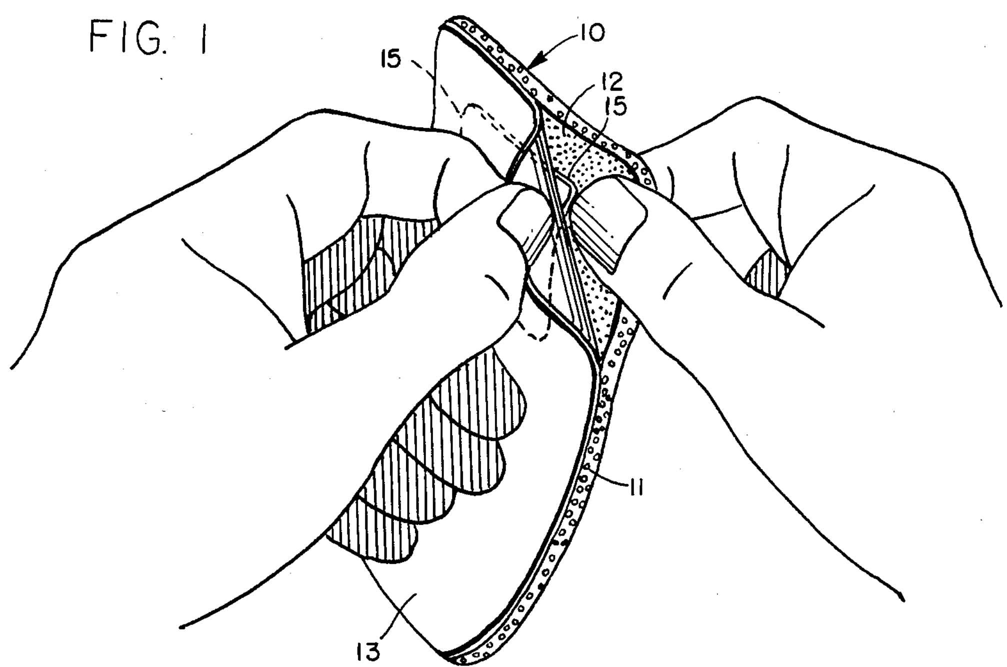
FIG. 1 is a perspective view of a device embodying the invention, the device being shown as a cover sheet is being peeled back to expose its adhesive surface.
Figure 2:
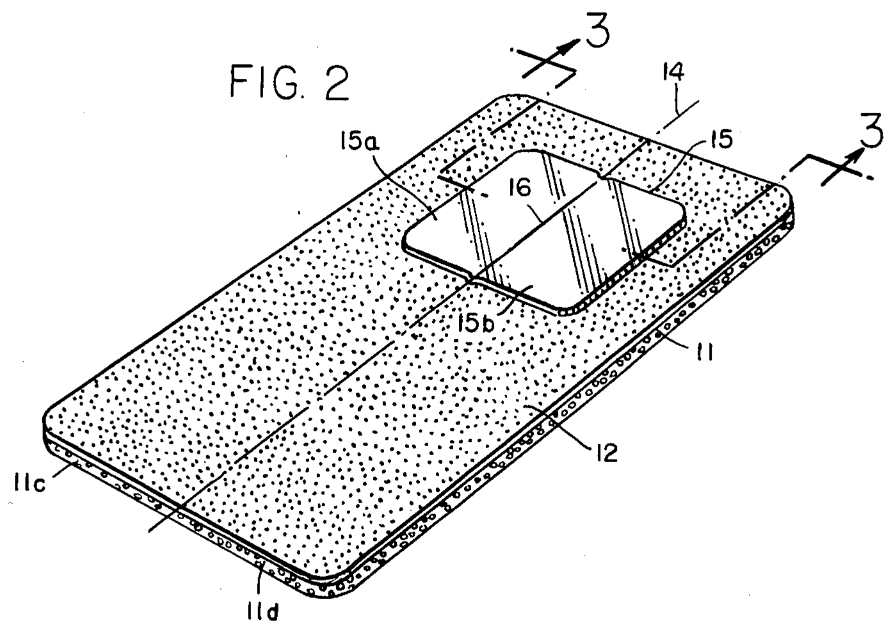
FIG. 2 is a perspective view of the device with the cover sheet removed.
Figure 3:
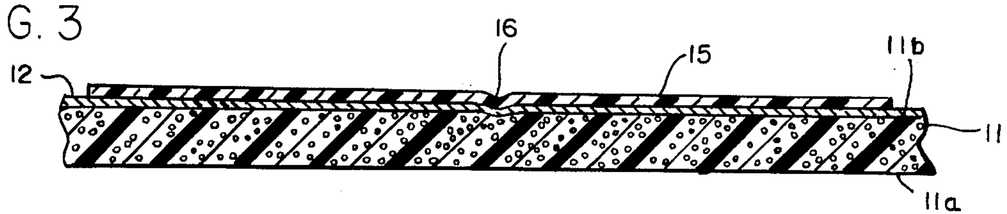
FIG. 3 is an enlarged vertical sectional view taken along line 3—3 of FIG. 2.

Referring to FIGS. 1–3 of the drawings, the numeral 10 generally designates a needle-stick injury prevention device including, as a main element thereof, a pad 11 formed of soft, readily-deformable sheet material. In the illustration given, the pad is of elongated rectangular shape. While the pad should be longer in one dimension than the other, the rectangular configuration, although preferred, is not essential. The pad is formed of a material that is readily foldable and generally compliant and, most advantageously, one that is impervious or at least highly resistant to the passage of fluids. A soft, closed-cell thermoplastic foam formed of polyethylene has been found particularly effective, but other materials having similar properties may be used. Alternatively, the pad may be formed of a fabric, such as a non-woven fabric that, preferably, has been treated to resist or retard fluid transmission.

The planar pad 11 has a lower surface **11*a* and an upper surface 11*b*, the latter being covered with a layer or coating 12 of pressure-sensitive adhesive. Acrylate-based adhesives have been found effective, but any suitable pressure-sensitive adhesive having a high degree of surface tack may be used. To protect the adhesive surface until the product is used, a removable cover sheet 13 extends over the entire adhesive-coated upper surface of the pad. The cover sheet, which may be formed of silicone-coated paper, may be readily stripped away from the adhesive coated surface when use of the device is required (FIG. 1**).

The elongated, planar pad 11 is readily foldable along its longitudinal midline 14. A protective shield or patch 15 of smooth, tough, imperforate, and relatively stiff sheet material is secured to the adhesive-coated upper surface of the pad near one end thereof. As shown most clearly in FIGS. 2 and 3, the shield 15 is provided with a straight, predetermined fold line 16 that registers with the midline of the pad and that helps direct and control upward folding of the side sections **15*a* and 15*b* when the device is in use. In the preferred form shown, the shield's fold line 16 is defined by a crease or score, but it will be understood that such a fold line might also be defined or supplemented by other means such as by an imprint or other indicia, or by linear molecular orientation of the shield's plastic material, or by some other variation in the composition or thickness along the fold line of the shield. Most advantageously, the shield is secured to the pad by the same pressure-sensitive coating 12** that extends beyond the margins of the shield. It is to be noted that the pad has a surface area substantially larger than that of the shield so that the adhesive-coated upper surface of the pad provides a border zone that extends outwardly about the entire perimeter of the shield. If desired, the exposed surface of the shield may also be adhesive coated, although such coating is omitted in the embodiment illustrated.

The shield may be formed of a sheet of tough plastic material such as polycarbonate, although other polymeric materials having similar properties may be used. Alternatively, the shield may be formed of aluminum or other metals that may be readily folded along a line 16. The thickness of the shield may be varied depending on the particular material selected; in the case of polycarbonate or similar polymeric materials, a thickness with the general range of 15 to 20 mils is believed particularly effective.

Figure 4:
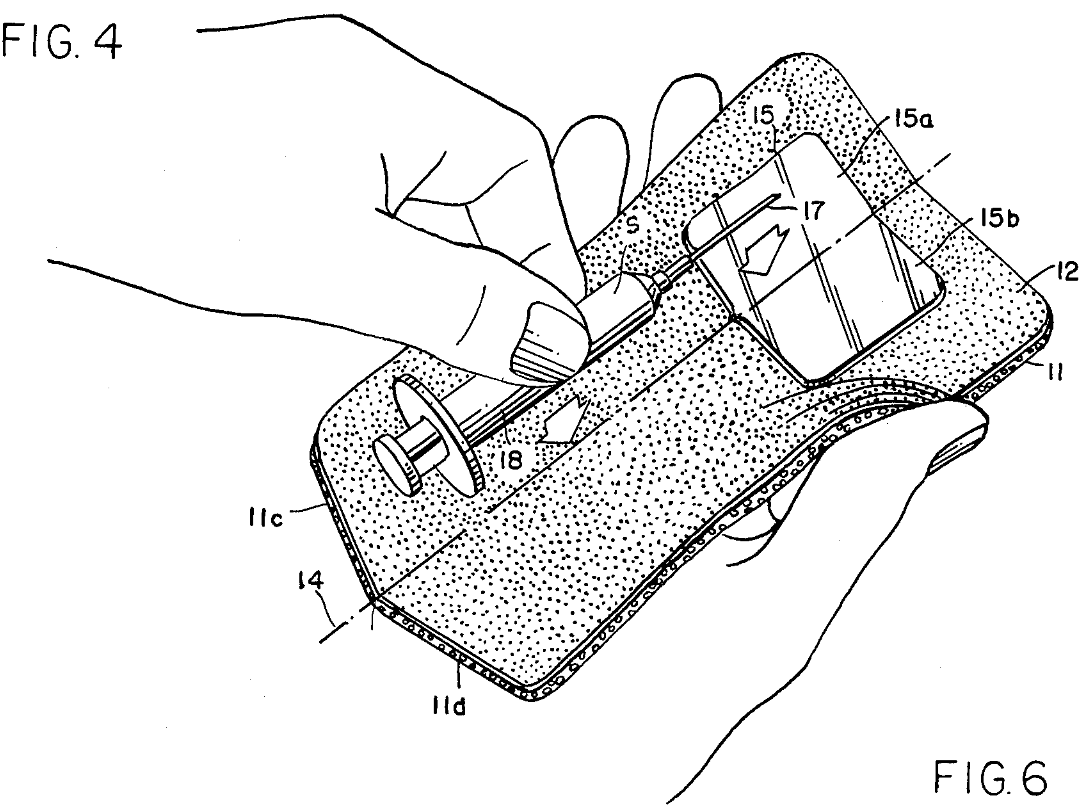
FIG. 4 is a perspective view illustrating a first step in the use of the device.
Figure 5:
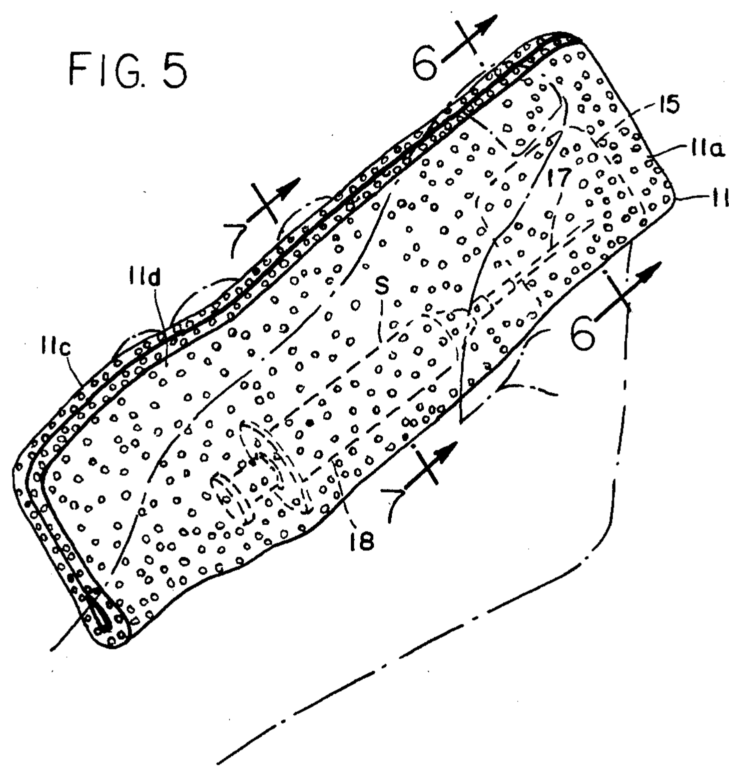
FIG. 5 is a perspective view illustrating a later step in the use of the device.
Figure 7:
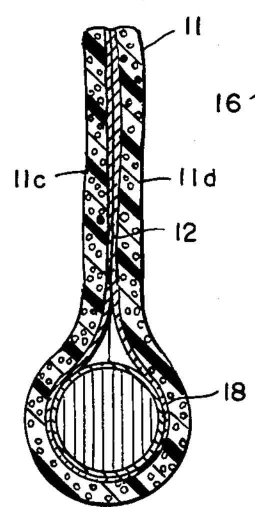
FIG. 7 is an enlarged cross sectional view taken along line 7—7 of FIG. 5.

The size of the pad may also be varied, although it is important that it be sufficient to permit a standard syringe S to be sealed between the pad's side or lateral sections **11*c* and 11*d* when the pad is folded along its midline 14 as indicated in FIGS. 4 and 5**. Also, the pad should be narrow enough to permit it to be folded using one hand—the width should therefore not exceed the maximum finger span of a typical user. In general, the pad should have a width within the range of about 5 to 20 centimeters, preferably about 8 to 12 centimeters, and a length at least as great as its width.

In use of the device, the cover sheet 13 is first removed (FIG. 1) and the pad is then held in one hand with the adhesive layer 12 facing upwardly and with the shield or patch 15 at the end of the pad pointing away from the user (FIG. 4). The user's fingertips are therefore disposed beneath or to each side of the shield. A used syringe is placed on the adhesive surface 12 with the axis of the syringe aligned with the midline 14 of the pad and with the tip of needle 17 overlying the shield's fold line 16 and well within the peripheral limits of the shield. Once the syringe barrel 18 contacts the adhesive 12, the syringe is immobilized upon the upper surface of the pad. The user then simply closes the fingers of the hand supporting the pad, causing the side sections **11*c* and 11*b* of the pad to fold together along line 14. The side sections 15*a* and 15*b* of the shield also fold together to entrap the needle 17 therebetween. Where the pad is formed of plastic foam, the textured lower surface 11*a*** helps insure that the pad will not slip or shift in the user's hand as it is folded. The compliance of the material from which the soft, deformable pad is formed also assists in that respect.

Figure 6:
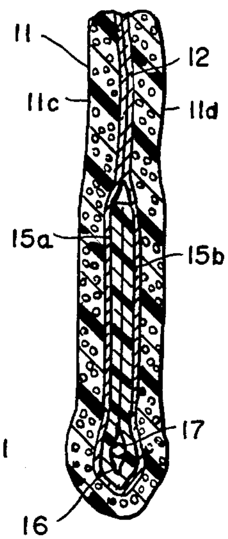
FIG. 6 is an enlarged cross sectional view taken along line 6—6 of FIG. 5.

When the pad is fully folded, the needle 17 of the syringe is encased between side sections **15*a* and 15*b* of the shield in close proximity to fold line 16. Lateral movement of the needle is effectively prevented by side sections 15*a*** and 15*b*, and axial movement is prevented by the adhesive coating 12 that immobilizes the syringe between the walls of the folded pad. Separation or unfolding of the shield is prevented by the portions of the pad extending beyond the borders of the shield, such portions being adhesively secured together as indicated in FIGS. 5 and 6. It has also been found that the folding of the shield along line 16 has a rigidifying effect which, combined with the shield's doubled thickness, helps insure that the needle 17 will remain securely encased within the folded shield.

In the preferred embodiment depicted in the drawings, the adhesive-coated pad projects outwardly beyond the entire perimeter of the shield 15. While it is important that the adhesive coating of the pad extend laterally beyond the side portions **15*a* and 15*b* of the shield and also beyond the distal edge of the shield (i.e., the edge toward which the tip of the needle 17 projects when the syringe is supported as in FIG. 4**), it is believed apparent that the adhesive coating might be omitted from areas of the larger portion of the pad that wraps about the barrel of the syringe without necessarily compromising the effectiveness of the device in retaining the syringe and its needle and in eliminating or at least reducing risks of needle-stick injury.

While in the foregoing I have disclosed an embodiment of the invention in considerable detail for purposes of illustration, it will be understood by those skilled in the art that many of these details may be varied without departing from the spirit and scope of the invention.

I claim:

1. A needle-stick injury prevention device comprising a pad of soft, foldable sheet material having upper and lower surfaces and having a pair of lateral sections disposed on opposite sides of the midline thereof; a coating of pressure-sensitive adhesive over said upper surface; and a protective shield of tough, flexible, imperforate sheet material secured to a portion of said upper surface; said shield having a straight, predetermined, centrally-disposed fold line aligned with said midline and delineating a pair of side sections of said shield foldable upwardly towards each other along said fold line; said pad having a surface area substantially larger than that of said shield with said adhesive-coated upper surface defining a border zone extending beyond the perimeter of said shield.

2. The device of claim 1 in which said fold line is defined by a preformed crease in said shield.

3. The device of claims 1 or 2 in which said shield is secured to said pad by said coating of pressure-sensitive adhesive.

4. The device of claims 1 or 2 in which said shield is formed of smooth, relatively stiff plastic material.

5. The device of claims 1 or 2 in which said shield is formed of metal.

6. The device of claims 1 or 2 in which said pad is formed of plastic foam.

7. The device of claim 6 in which said plastic foam is closed-cell foam and is generally fluid-impermeable.

8. The device of claim 1 in which said adhesive coating and said shield are covered by a removable cover sheet.

9. The device of claim 1 in which said pad is elongated and is generally rectangular in shape.

10. The device of claim 1 in which said pad has a width in the range of 5 to 20 centimeters.

11. The device of claim 10 in which said pad has a width within the range of about 8 to 12 centimeters.

12. The device of claims 1 or 2 in which said shield is disposed closer to one end of said pad than to the other end thereof.

13. The device of claims 1 or 2 in which said adhesive border zone extends outwardly about the entire perimeter of said shield.

14. A method of encasing a used needle-equipped syringe to prevent needle-stick injury, comprising the steps of adhering the barrel of a used syringe to an adhesive coating along the upper surface of a pad of soft, foldable material with the axis of said syringe extending along the midline of said pad and with the needle tip of said syringe overlying a protective patch of tough, foldable, imperforate sheet material secured to said upper surface; then folding said pad and said patch along said midline, while said syringe is immobilized by said adhesive coating, to encase said needle tip between a pair of side sections of said patch and to urge portions of said adhesive-coated upper surface of said pad into sealing contact with each other about said syringe and about the periphery of said folded patch.

* * * * *